US010863960B2

(12) United States Patent
Ohishi

(10) Patent No.: US 10,863,960 B2
(45) Date of Patent: Dec. 15, 2020

(54) X-RAY DIAGNOSIS APPARATUS

(71) Applicant: Toshiba Medical Systems Corporation, Otawara (JP)

(72) Inventor: Satoru Ohishi, Otawara (JP)

(73) Assignee: Canon Medical Systems Corporation, Otawara (JP)

( * ) Notice: Subject to any disclaimer, the term of this patent is extended or adjusted under 35 U.S.C. 154(b) by 862 days.

(21) Appl. No.: 14/551,921

(22) Filed: Nov. 24, 2014

(65) Prior Publication Data
US 2015/0150527 A1  Jun. 4, 2015

(30) Foreign Application Priority Data

Dec. 3, 2013  (JP) .................................. 2013-250596

(51) Int. Cl.
*A61B 6/00* (2006.01)
*A61B 6/02* (2006.01)
*A61B 6/12* (2006.01)

(52) U.S. Cl.
CPC .............. *A61B 6/504* (2013.01); *A61B 6/022* (2013.01); *A61B 6/12* (2013.01); *A61B 6/4441* (2013.01); *A61B 6/487* (2013.01)

(58) Field of Classification Search
CPC ......... A61B 6/022; A61B 6/12; A61B 6/4441; A61B 6/487; A61B 6/504
See application file for complete search history.

(56) References Cited

U.S. PATENT DOCUMENTS

| 6,529,766 | B1 * | 3/2003 | Guendel .................. A61B 6/12 600/411 |
| 8,046,051 | B2 * | 10/2011 | Homan ................ A61B 6/4441 382/128 |
| 2002/0181645 | A1 * | 12/2002 | Bruder ................... A61B 6/481 378/8 |
| 2013/0089183 | A1 * | 4/2013 | Sura ..................... A61B 6/4225 378/98.2 |

FOREIGN PATENT DOCUMENTS

JP         2012-249960         12/2012

* cited by examiner

Primary Examiner — Amelie R Davis
(74) Attorney, Agent, or Firm — Oblon, McClelland, Maier & Neustadt, L.L.P.

(57) ABSTRACT

According to one embodiment, apparatus includes imaging unit, generator, position specifier, direction specifier and angle setter. Imaging unit images object into which a device is inserted, from first and second direction. Generator generates first image data and second image data each corresponding to first and second direction. Position specifier specifies position of the device based on first and second image data. Direction specifier specifies moving direction of the device based on positions of the device specified by position specifier. Angle setter sets first angle corresponding to first direction and second angle corresponding to second direction in accordance with moving direction of the device.

16 Claims, 11 Drawing Sheets

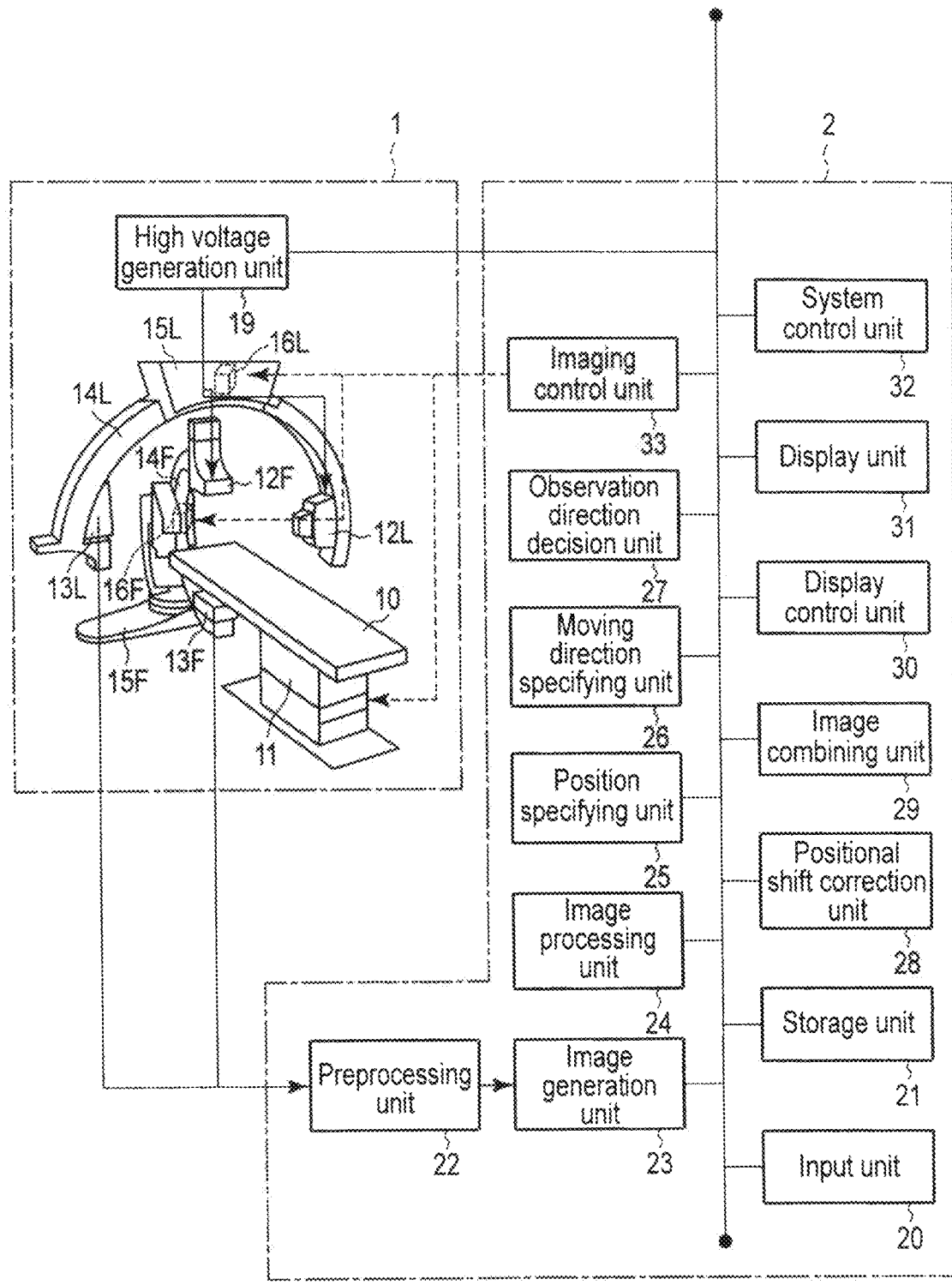
F I G. 1

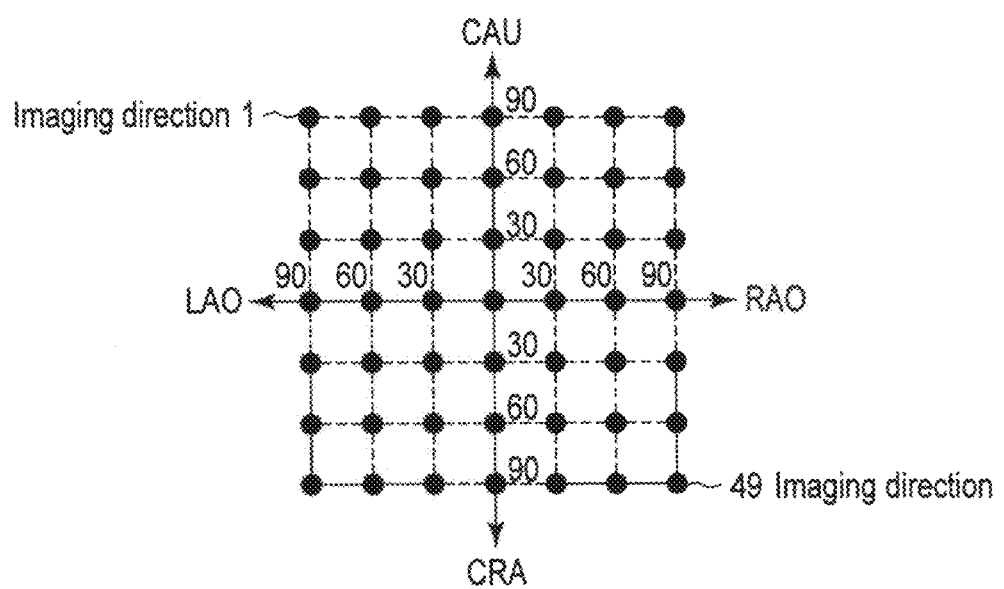
F I G. 7

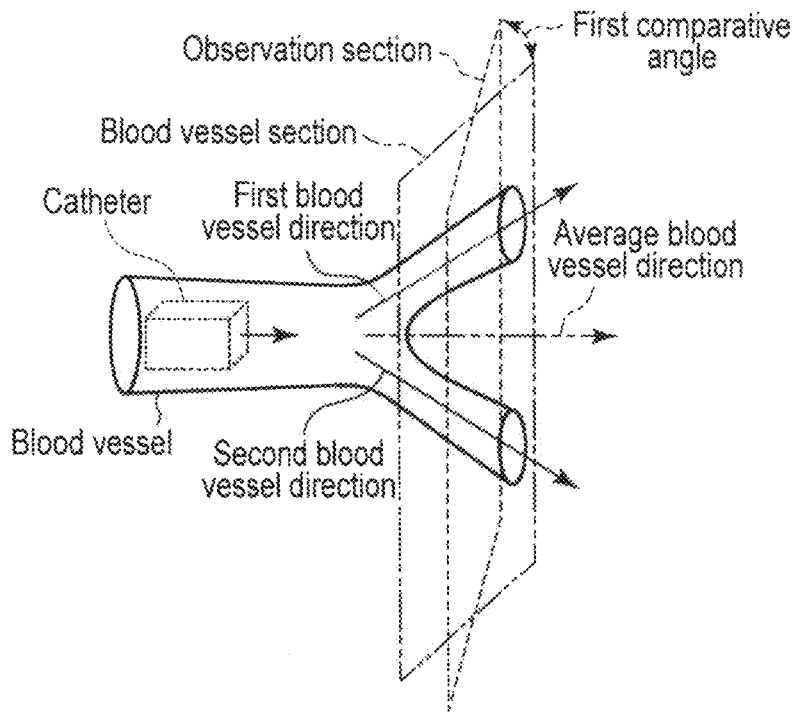
F I G. 9A
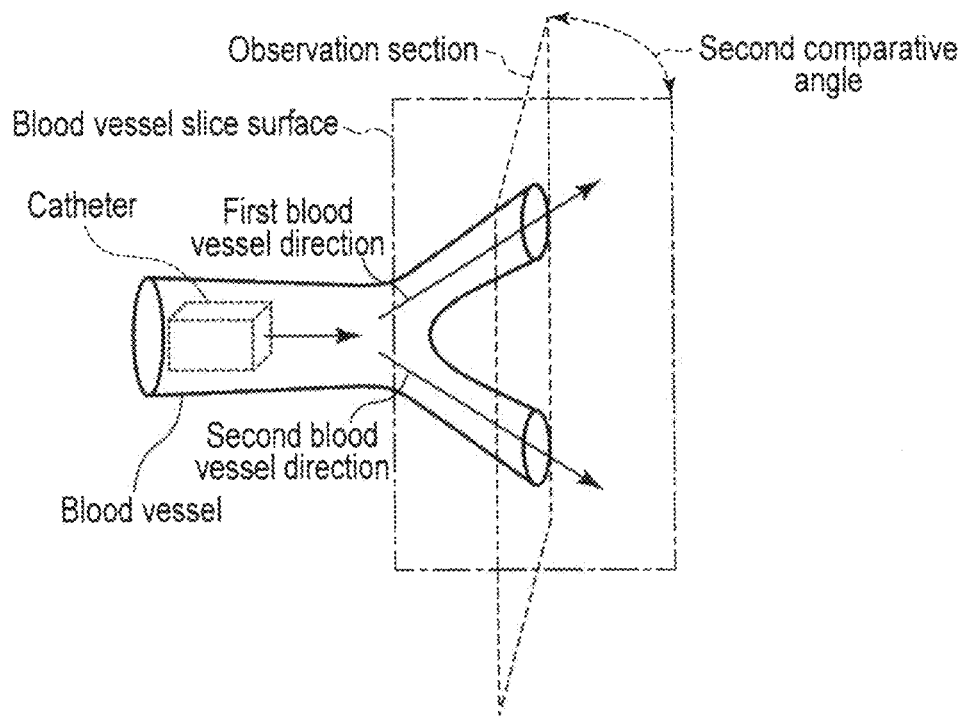
F I G. 9B

X-RAY DIAGNOSIS APPARATUS

CROSS-REFERENCE TO RELATED APPLICATIONS

This application is based upon and claims the benefit of priority from the Japanese Patent Application No. 2013-250596, filed Dec. 3, 2013, the entire contents of which are incorporated herein by reference.

FIELD

Embodiments described herein relate generally to an X-ray diagnosis apparatus.

BACKGROUND

An X-ray diagnosis apparatus provides a user with a large amount of various information concerning an object in the form of images and the like. The X-ray diagnosis apparatus plays an important role in medical practices such as disease diagnosis, treatment, and operation planning.

X-ray diagnosis apparatuses include, for example, biplane X-ray imaging apparatuses and stereoscopic X-ray imaging apparatuses. These apparatuses can simultaneously image an object from two directions, and hence can cope with medical practices such as complicated procedures and treatments better than apparatuses which can perform imaging only from one direction.

For example, in the field of catheter treatment, a technique called 3D road mapping is known. 3D road mapping is a technique of reconstructing a catheter image from object images acquired in real time by a biplane X-ray imaging apparatus or stereoscopic X-ray imaging apparatus and superimposing/displaying the reconstructed catheter image and a 3D blood vessel image. This technique allows the user to see in real time how a catheter moves in a blood vessel. Highly accurate treatments can therefore be expected.

If, however, one of the two imaging directions in a biplane X-ray imaging apparatus or stereoscopic X-ray imaging apparatus and the moving direction of a catheter approach in parallel, the positional accuracy of a reconstructed image of the catheter deteriorates.

BRIEF DESCRIPTION OF THE DRAWINGS

FIG. 1 is a block diagram showing an example of a biplane X-ray imaging apparatus according to the first embodiment;

FIG. 7 is a view showing an example of an imaging angle map template stored in a storage unit 21 of a biplane X-ray imaging apparatus according to the second embodiment;

FIGS. 9A and 9B are views for explaining a first comparative angle and a second comparative angle;

DETAILED DESCRIPTION

Figure 2:
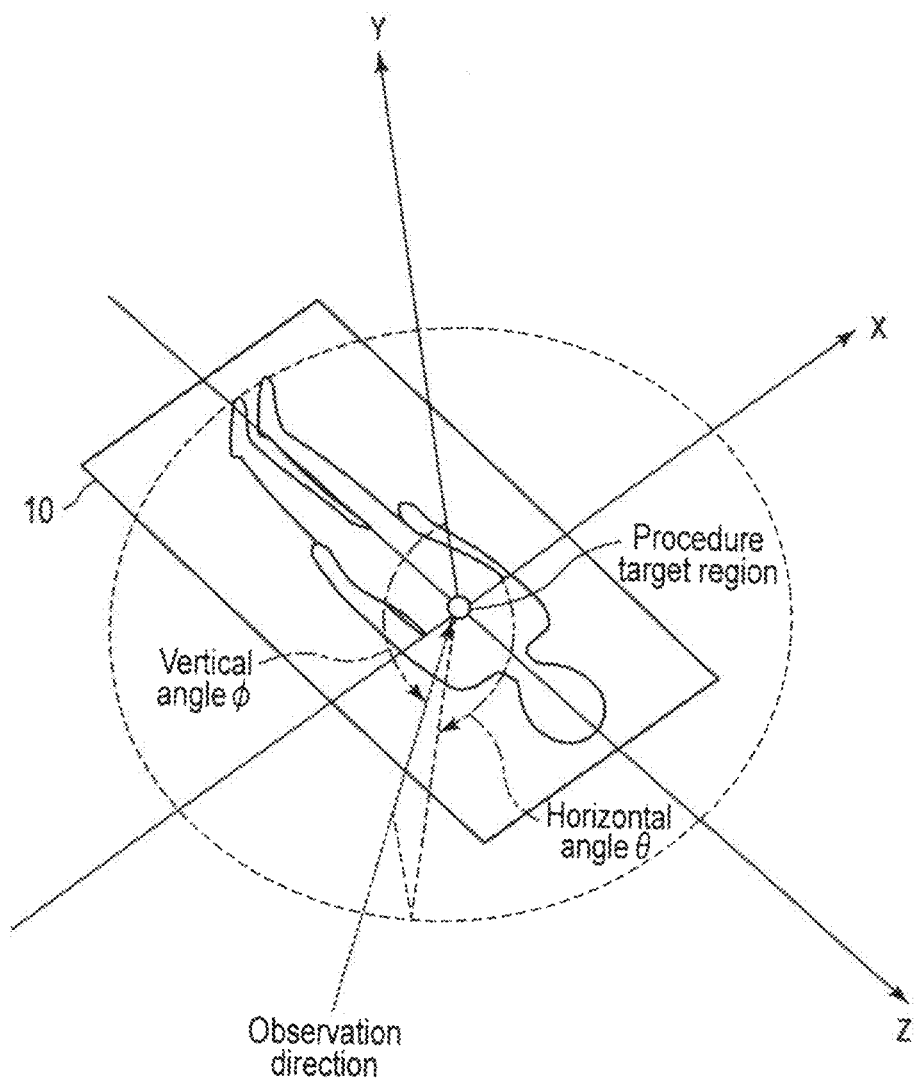
FIG. 2 is a view for explaining an observation direction and an observation angle.

In general, according to one embodiment, an X-ray diagnosis apparatus includes an imaging unit, a driving unit, an image generator, a position specifying unit, a moving direction specifying unit and an angle setting unit.

The imaging unit images an object into which a device is inserted, from a first imaging direction and a second imaging direction. The driving unit drives the imaging unit. The image generator generates first image data corresponding to the first imaging direction and second image data corresponding to the second imaging direction based on an output from the imaging unit. The position specifying unit specifies a position of the device based on the first image data and the second image data. The moving direction specifying unit specifies a moving direction of the device based on a plurality of positions of the device specified by the position specifying unit. The angle setting unit sets a first imaging angle corresponding to the first imaging direction and a second imaging angle corresponding to the second imaging direction in accordance with the moving direction of the device.

A plurality of embodiments will be described below with reference to the accompanying drawings. The present invention can be applied to an X-ray diagnosis apparatus including a plurality of X-ray tubes. For the sake of descriptive simplicity, the first, second, and third embodiments will exemplify biplane X-ray imaging apparatuses. The fourth embodiment will exemplify a stereoscopic X-ray imaging apparatus. Assume that a device (to be simply referred to as a catheter hereinafter) used for treatment, such as a catheter and a guide wire, has been inserted in an object. Note that the same reference numerals denote constituent elements common to the accompanying drawings, and a repetitive description will be made only when required.

First Embodiment

FIG. 1 is a block diagram showing an example of a biplane X-ray imaging apparatus according to the first embodiment. The biplane X-ray imaging apparatus shown in FIG. 1 includes an imaging apparatus 1 (imaging unit 1) and a data processing apparatus 2. The imaging apparatus 1 includes a top 10, a bed 11, a high voltage generation unit 19, and a plurality of imaging systems.

The bed 11 movably supports the top 10 on which an object is placed. The bed 11 includes a bed driving unit (not shown). The top 10 moves when the bed driving unit is driven under the control of an imaging control unit 33 (to be described later).

The plurality of imaging systems include, for example, a first imaging system of a front surface system (frontal: F) and a second imaging system of a side surface system (lateral: L). The first imaging system includes an X-ray focus 12F, an X-ray detector 13F, a C-arm 14F, a C-arm support mechanism 15F, and a C-arm driving unit 16F. The second imaging system includes an X-ray focus 12L, an X-ray detector 13L, a C-arm 14L, a C-arm support mechanism 15L, and a C-arm driving unit 16L. The C-arm driving unit 16F and the C-arm driving unit 16L are together called a mechanism driving unit 16.

The C-arm 14F holds, at its one end, the X-ray focus 12F. The X-ray focus 12F is a vacuum tube which generates X-rays. The X-ray focus 12F generates X-rays from the X-ray focus upon receiving a high voltage (tube voltage) and a tube current from the high voltage generation unit 19. The X-ray focus 12F has a radiation window for radiating generated X-rays. An X-ray collimator is attached to the radiation window of the X-ray focus 12F. The X-ray collimator can adjust an X-ray irradiation field on the detection surface of the X-ray detector 13F. Adjusting the X-ray irradiation field with the X-ray collimator can reduce unnecessary exposure of an object.

The C-arm 14F holds, at its other end, the X-ray detector 13F so as to make it face the X-ray focus 12F. The X-ray detector 13F includes a plurality of X-ray detection elements. The plurality of X-ray detection elements are arranged in a two-dimensional array. The detector in the two-dimensional array is called an FPD (Flat Panel Detector). Each element of the FPD detects the X-rays emitted from the X-ray focus 12F and transmitted through an object. Each element of the FPD outputs an electrical signal corresponding to a detected X-ray intensity.

The C-arm 14F rotatably supports the C-arm support mechanism 15F. The C-arm support mechanism 15F includes the C-arm driving unit 16F for rotating the C-arm 14F. The C-arm 14F is rotated about a plurality of rotation axes by driving the C-arm driving unit 16F under the control of the imaging control unit 33.

The above description of each constituent element of the first imaging system applies to the second imaging system. The C-arm support mechanism 15F of the first imaging system (front surface system) is, for example, of a floor-standing type that holds the C-arm 14F with a floor-standing mechanism. On the other hand, the C-arm support mechanism 15L of the second imaging system (side surface system) is, for example, of a ceiling suspended system that holds the C-arm 14L by suspending it from the ceiling.

The data processing apparatus 2 includes an input unit 20, a storage unit 21, a pre-processing unit 22, an image generation unit 23, an image processing unit 24, a position specifying unit 25, a moving direction specifying unit 26, an observation direction decision unit 27, a positional shift correction unit 28, an image combining unit 29, a display control unit 30, a display unit 31, a system control unit 32, and an imaging control unit 33.

The input unit 20 functions as an interface for inputting instruction information from the user to this biplane X-ray imaging apparatus. Instruction information includes, for example, moving instructions to the first and second imaging systems, a setting instruction for imaging conditions, and registration instructions for a plurality of observation directions (a left-eye viewing direction and a right-eye viewing direction), a parallax angle, and an imaging angle difference.

The input unit 20 includes an operation console for moving the first and second imaging systems. The operation console includes buttons, a handle, and a trackball. The user can move these imaging systems to desired imaging positions by operating the operation console.

In addition, the input unit 20 includes a change switch for changing an observation direction, a function ON switch for turning on the observation direction changing function, and a function OFF switch for turning off the observation direction changing function. The user can register a parallax angle, an imaging angle difference, and a plurality of observation directions by using the input unit 20.

FIG. 2 is a view for explaining an observation direction and an observation angle. Referring to FIG. 2, an axis along the short axis of the top 10 is defined as the X-axis, an axis along the long axis is defined as the Z-axis, and an axis perpendicular to the X-axis and the Z-axis is defined as the Y-axis. An observation direction is a direction in which the user wants to image an object. An observation angle corresponding to an observation direction is expressed by a horizontal angle θ defined with respect to the X-axis and a vertical angle φ defined with respect to the Y-axis.

Figure 3:
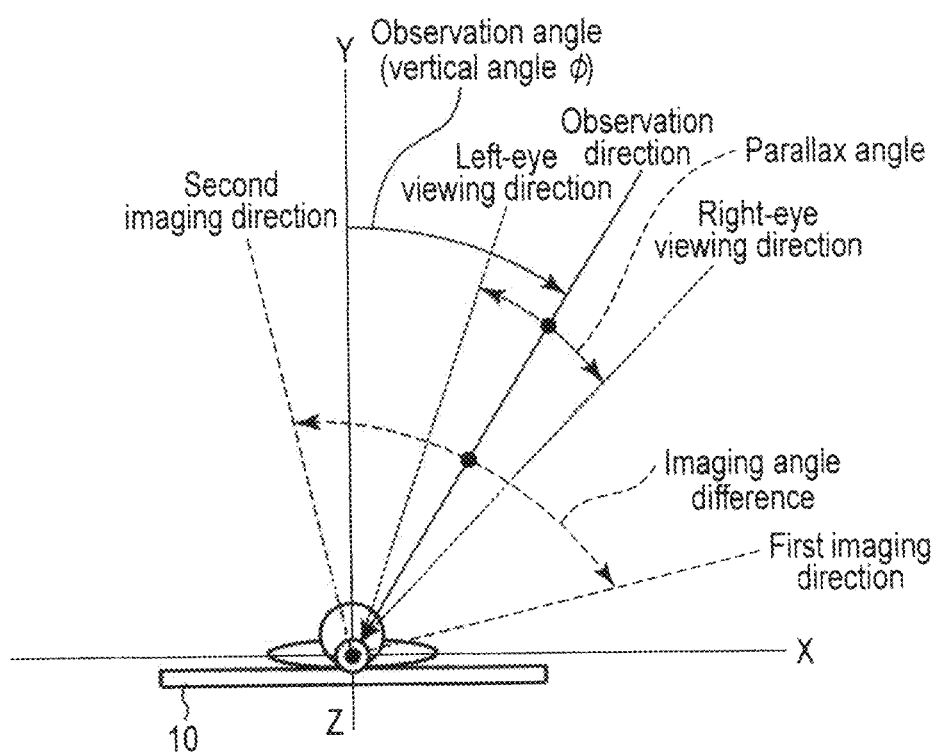
FIG. 3 is a view showing an example of the relationship between observation angle, imaging angle difference, and parallax angle.

FIG. 3 is a view showing an example of the relationship between observation angle, imaging angle difference, and parallax angle. A first imaging direction corresponds to the imaging direction of the first imaging system. A second imaging direction corresponds to the imaging direction of the second imaging system.

Referring to FIG. 3, consider a first imaging angle corresponding to the first imaging direction and a second imaging angle corresponding to the second imaging direction. As shown in FIG. 3, the first and second imaging angles have a predetermined angle width (imaging angle difference). An imaging angle difference is set in advance to about 90°. If the imaging angle difference is about 90°, the first imaging direction is perpendicular to the second imaging direction. For example, the angle defined by the first imaging angle and the observation direction is equal to the angle defined by the second imaging angle and the observation direction.

A predetermined relationship is set in advance between the first imaging direction, the second imaging direction, and the observation direction. For example, when a procedure target region, an observation direction for the region, and the top and bottom of an image to be displayed on the display unit 31 are set, the first and second imaging directions are automatically set. For example, the first and second imaging directions are set on a plane which is perpendicular to the set top and bottom of the image and includes an observation direction.

The right-eye viewing direction corresponds to a direction in which the user visually recognizes the display unit 31 with his/her right eye at a position a predetermined distance away from the display unit 31. The left-eye viewing direction corresponds to a direction in which the user visually recognizes the display unit 31 with his/her left eye at a position a predetermined distance away from the display unit 31. The user can stereoscopically recognize an object from an observation direction by seeing the object from the right-eye viewing direction with his/her right eye and from the left-eye viewing direction with his/her left eye.

A predetermined relationship is set in advance between a right-eye viewing direction, a left-eye viewing direction, and an observation direction. Referring to FIG. 3, the right-eye viewing direction corresponds to the right-eye viewing angle, and the left-eye viewing direction corresponds to the left-eye viewing angle. As shown in FIG. 3, for example, the angle defined by the right-eye viewing angle and the observation angle is equal to the angle defined by the left-eye viewing angle and the observation angle. In addition, the angle defined by the right-eye viewing angle and the left-eye viewing angle is a predetermined angle (parallax angle). As described above, when an observation direction is registered, a right-eye viewing direction and a left-eye viewing direction are automatically registered.

Methods of registering a plurality of observation directions include, for example, the following methods:

1) The user can designate either the first imaging angle or the second imaging angle as a right-eye viewing direction or a left-eye viewing direction. A normal imaging angle called a working angle is an angle optimal for a procedure.

2) The user manually registers a plurality of observation directions in the system. For example, in this registration process, a model image of the object placed on the top 10 is displayed on the display unit 31. The user can register an observation direction on the displayed model image.

3) The user selects a region subjected to a procedure. The storage unit 21 stores in advance the data of a plurality of observation direction sets/imaging angle sets respectively corresponding to a plurality of regions. An observation direction set is a data set concerning a plurality of observation directions registered in advance in correspondence with a region. An imaging angle set is a data set including the first and second imaging angles.

When the user selects a region subjected to a procedure, the data of an observation direction set/imaging angle set corresponding to the selected region is read out from the storage unit 21. A plurality of observation directions/imaging angles are then automatically registered in the system.

In the case of 3), the user may input not only a region subjected to a procedure but also other information (e.g., the age, physique, imaging posture of an object and the vertical direction of an image). An observation direction set is read out from the storage unit 21 in accordance with the input information. Note that it is possible to change a plurality of imaging directions included in the observation direction set registered in the storage unit 21 in advance by using the input unit 20, as needed.

The storage unit 21 is a semiconductor storage device such as a flash SSD (Solid State Drive), HDD (Hard Disk Drive), or the like. The storage unit 21 stores the data of the image generated by the image generation unit 23, data concerning the image processed by the image processing unit 24, parallax angle data, imaging angle difference data, and the data of a reference angle to be described later, and data concerning a plurality of observation direction sets.

The storage unit 21 stores the data of each of a plurality of observation direction sets in association with a corresponding region (landmark structure). In addition, the storage unit 21 stores the data of a warning message for notifying the user of an observation direction suitable for the current observation direction.

The pre-processing unit 22 generates projection data by executing pre-processing for the electrical signal output from the X-ray detector 13F. Pre-processing includes, for example, amplification processing for an electrical signal, A/D conversion processing of changing an electrical signal to digital data, sensitivity nonuniformity correction processing between channels, and the processing of correcting an extreme decrease in signal intensity or signal dropout due to an X-ray absorber, mainly a metal portion. Projection data is stored in the storage unit 21 in association with data representing a channel number, a detection element column number, and an imaging angle.

The image generation unit 23 generates the data of an X-ray image based on the pre-processed projection data. More specifically, the image generation unit 23 generates a first fluoroscopic image corresponding to the first imaging direction and a second fluoroscopic image corresponding to the second imaging direction. The image generation unit 23 also generates the data of a plurality of X-ray images respectively corresponding to a plurality of imaging angles.

X-ray images include, for example, an X-ray image concerning an object before the injection of a contrast medium and an X-ray image concerning the object after the injection of the contrast medium. One of the first and second imaging systems generates the X-ray image concerning the object before the injection of the contrast medium and the X-ray image concerning the object after the injection of the contrast medium by imaging the object while rotating around the object. The pixel value assigned to each pixel constituting the image generated by the image generation unit 23 is a value or the like corresponding to an X-ray attenuation coefficient concerning a substance on an X-ray transmission path.

The image processing unit 24 executes various types of image processing for the image data generated by the image generation unit 23. More specifically, the image processing unit 24 generates blood vessel image data with an enhanced blood vessel by obtaining the difference between an X-ray image before the injection of a contrast medium and an X-ray image after the injection of the contrast medium, which are obtained at the same imaging angle.

The image processing unit 24 then generates 3D blood vessel image data by executing three-dimensional reconstruction processing for a plurality of blood vessel image data respectively corresponding to a plurality of imaging angles. For example, the Feldkamp reconstruction method or the like can be used as a three-dimensional reconstruction algorithm for obtaining 3D blood vessel image data from a plurality of blood vessel image data.

The image processing unit 24 generates right-eye blood vessel image data and left-eye blood vessel image data based on 3D blood vessel image data. The right-eye blood vessel image data corresponds to the right-eye viewing direction. Likewise, the left-eye blood vessel image data corresponds to the left-eye viewing direction.

In this embodiment, 3D blood vessel image data is generated based on the blood vessel image data obtained by the biplane X-ray imaging apparatus. 3D blood vessel image data is not limited to this, and may be obtained by another modality such as an X-ray CT apparatus or MRI apparatus and stored in the storage unit 21 in advance.

The positional shift correction unit 28 generates projection data by projecting the images obtained by the X-ray CT apparatus and the MRI apparatus as if they were obtained from the first and second imaging angles. The positional shift correction unit 28 compares these projection data with corresponding obtained data and corrects the positional shift of the X-ray CT image or MRI image based on the comparison result. As a correction processing method, for example, a cross-correlation method or phase-only correlation method is used. If a target image is an MRI image, the positional shift correction unit 28 executes projection processing upon replacing the MRI image with information obtained as if it were imaged by the X-ray CT apparatus, based on mutual information.

The image processing unit 24 generates a catheter image including a moving image of the catheter which is extracted by subtracting a fluoroscopic image after a catheter operation from a fluoroscopic image before a catheter operation. The fluoroscopic image before a catheter operation may be a mask image generated by averaging a plurality of fluoroscopic images.

The image processing unit 24 generates 3D catheter image data by executing three-dimensional reconstruction processing for both a first catheter image corresponding to the first imaging direction and a second catheter image corresponding to the second imaging direction. For example, a geometrical reconstruction method or iterative reconstruction with a prior knowledge can be used as a three-dimensional reconstruction algorithm for obtaining 3D catheter image data from a plurality of catheter image data. As a prior knowledge, the three-dimensional continuity, volume, or the like of a signal can be used.

An example of the method of reconstructing an overall catheter image has been described so far. However, the present invention is not limited to this. A 3D catheter image is used to specify the moving direction of the catheter in a later description. That is, an image of the distal end portion of the catheter is required to specify the moving direction of the catheter. Therefore, the image processing unit 24 may extract an image of the distal end of the catheter from a catheter image and reconstruct only a distal end image. This makes it possible to reduce the load on data processing.

It is also possible to specify the moving direction of the catheter by extracting an image of the marker or the like attached to the distal end of the catheter from a catheter image and tracing a change in the position of the marker. As a marker, for example, the position sensor attached to the distal end of the catheter can be used. In addition, it is possible to extract an image of a guide wire which guides the catheter, instead of a blood vessel or catheter image, by image processing.

The image processing unit 24 generates right-eye catheter image data and left-eye catheter image data based on a 3D catheter image. The right-eye catheter image data corresponds to the right-eye viewing direction. Likewise, the left-eye catheter image data corresponds to the left-eye viewing direction.

The accuracy of an image of the distal end portion of the catheter reconstructed based on the first and second catheter images changes depending on the positional relationship between the first and second imaging directions relative to the moving direction of the catheter.

Figure 4A:
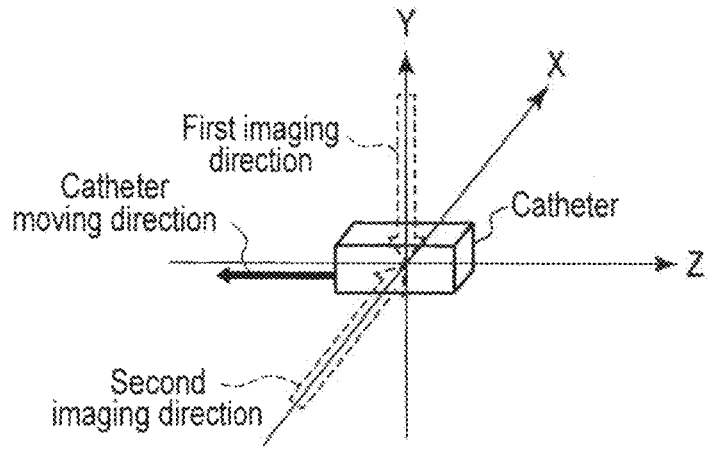
FIGS. 4A, 4B, and 4C are views each showing an example of the positional relationship between the moving direction of a catheter, a first imaging direction, and a second imaging direction.
Figure 4B:
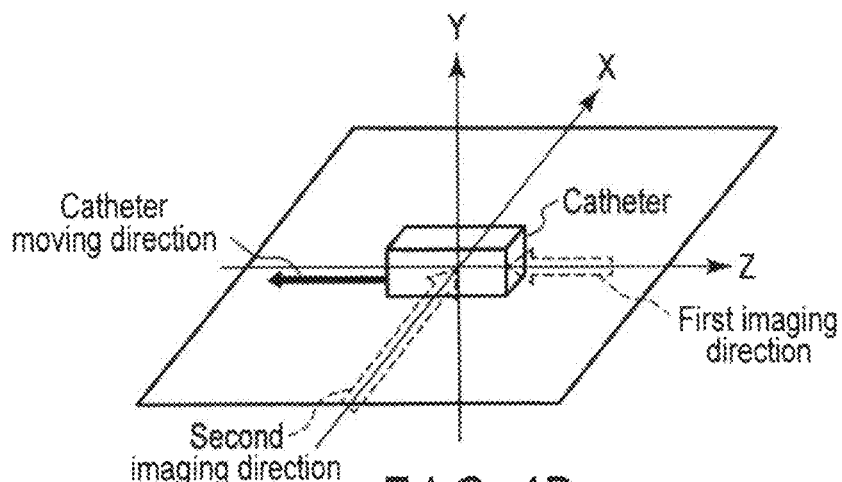
Figure 4C:
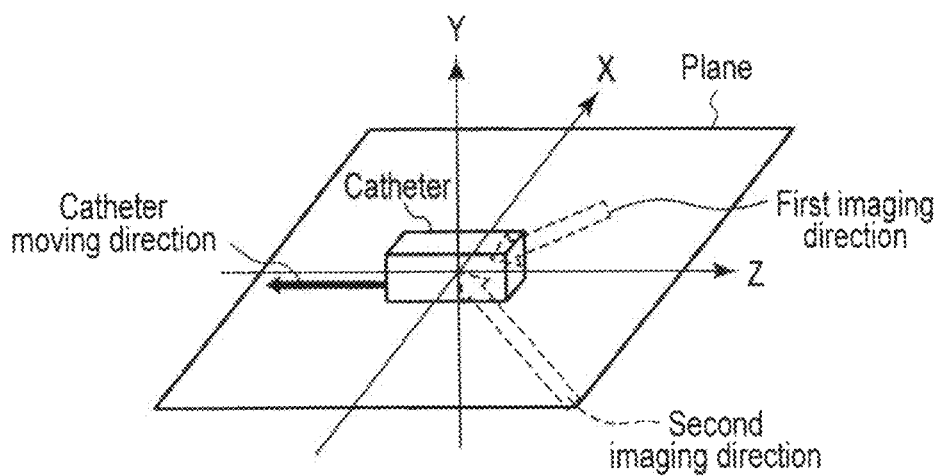

FIGS. 4A, 4B, and 4C are views each showing an example of the positional relationship between the moving direction of the catheter and the first and second imaging directions. FIGS. 4A, 4B, and 4C show three different imaging directions relative to the moving direction of the catheter. Assume that in FIGS. 4A, 4B, and 4C, the first and second imaging directions are set to be perpendicular to each other.

FIG. 4A shows an example in which both the first imaging direction and the second imaging direction are perpendicular to the moving direction of the catheter. Since both the first imaging direction and the second imaging direction are perpendicular to the moving direction of the catheter, it is possible to specify the position of the catheter from the first and second catheter images.

FIG. 4B shows an example in which although the second imaging direction is perpendicular to the moving direction of the catheter, the first imaging direction is almost parallel to the moving direction. Since the first imaging direction is almost parallel to the moving direction of the catheter, it is difficult to accurately specify the position of the catheter from the first catheter image. That is, the imaging direction shown in FIG. 4A makes it possible to more accurately reconstruct an image of the distal end portion of the catheter than the imaging direction shown in FIG. 4B.

FIG. 4C shows an example in which although neither the first imaging direction nor the second imaging direction is parallel to the moving direction of the catheter, a plane including the first and second imaging directions includes the moving direction of the catheter. Referring to FIG. 4C, neither the first imaging direction nor the second imaging direction is parallel to the moving direction of the catheter. Therefore, the imaging direction shown in FIG. 4C makes it possible to more accurately reconstruct an image of the distal end portion of the catheter than the imaging direction shown in FIG. 4B. However, the accuracy obtained by the imaging direction shown in FIG. 4C is lower than that obtained by the imaging direction shown in FIG. 4A.

From the above, in order to maintain the accuracy of the reconstruction of an image of the distal end portion of the catheter, the first and second imaging directions need to be perpendicular to the moving direction of the catheter or maintained at an angle nearly perpendicular to it.

The position specifying unit 25 specifies the position of the catheter based on the 3D catheter image data generated by the image processing unit 24.

The moving direction specifying unit 26 specifies the moving direction of the catheter based on the positions of the catheter imaged at different times, which are specified by the position specifying unit 25.

The observation direction decision unit 27 (also called an angle setting unit) specifies the direction of a blood vessel along the moving direction of the catheter specified by the moving direction specifying unit 26 by tracking the blood vessel in the moving direction. The observation direction decision unit 27 then selects one of a plurality of observation directions in accordance with the direction of the blood vessel.

More specifically, the observation direction decision unit 27 specifies a section (to be referred to as a blood vessel section hereinafter) perpendicular to a direction along the blood vessel. The observation direction decision unit 27 also specifies a section (to be referred to as an observation section hereinafter) including a straight line connecting the X-ray focus of the first imaging system and the central point of the detection surface of the X-ray detector 13F and a straight line connecting the X-ray focus of the second imaging system and the central point of the detection surface of the X-ray detector 13L. The observation direction decision unit 27 then specifies the angle (to be referred to as the comparative angle hereinafter) defined by the blood vessel section and the observation section.

If the comparative angle is 0°, the first and second imaging directions are almost perpendicular to the direction of the blood vessel along the moving direction of the catheter. If the comparative angle is 90°, the direction of the blood vessel along the moving direction of the catheter is almost parallel to a plane including the first and second imaging directions.

Figure 5A:
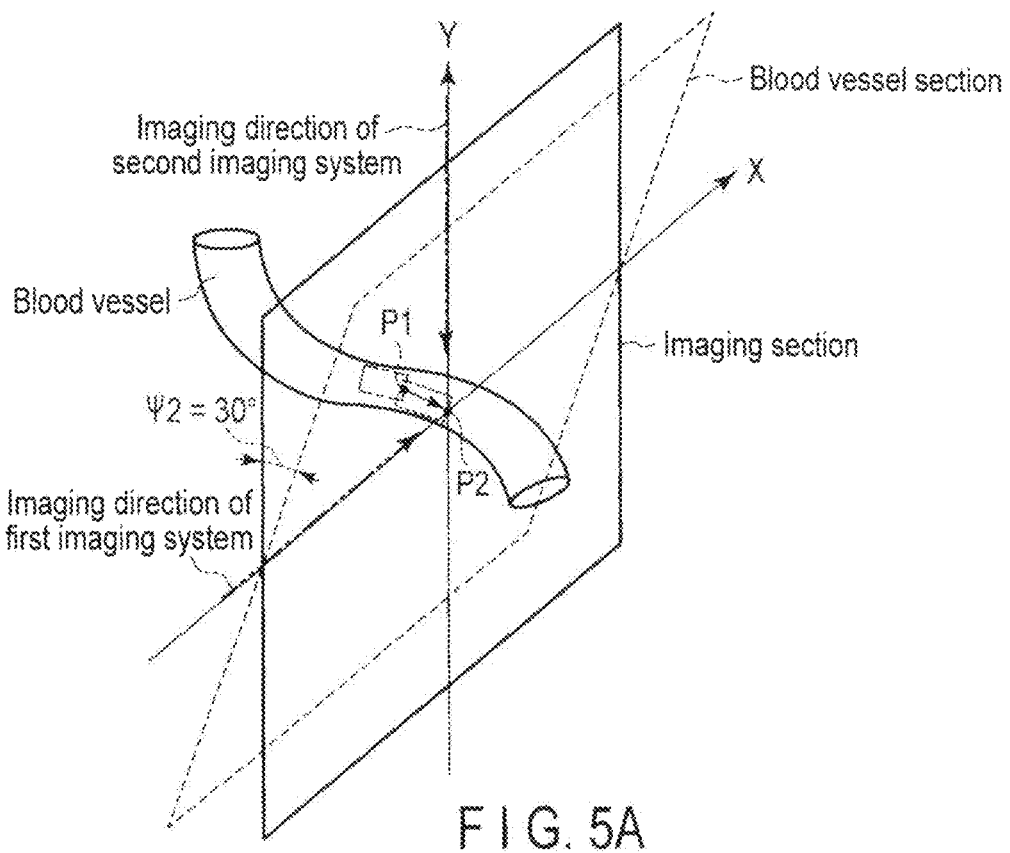
FIGS. 5A and 5B are views for explaining a blood vessel section, an observation section, and a comparative angle.
Figure 5B:
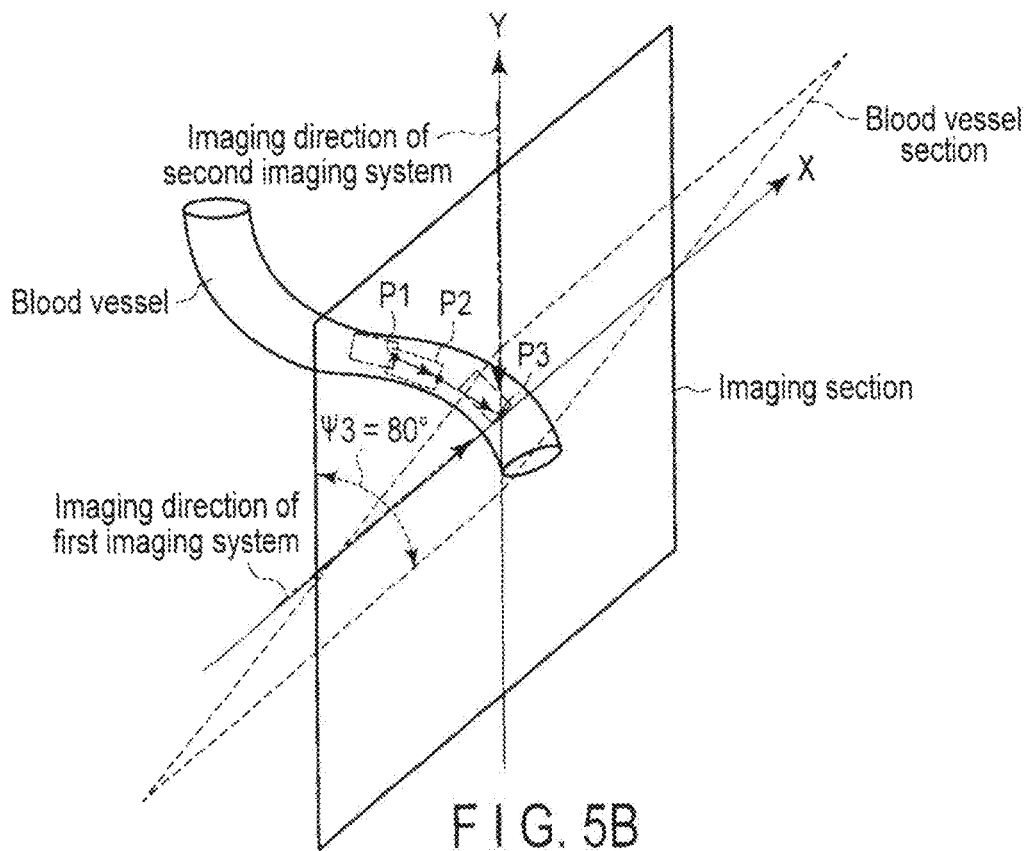

FIGS. 5A and 5B each are a view for explaining a blood vessel section, an observation section, and a comparative angle. FIGS. 5A and 5B schematically show how the catheter moves in the blood vessel. For the sake of descriptive simplicity, assume that the observation section is an X-Y plane. Assume also that a reference angle is 45°. The reference angle functions as a threshold. When the comparative angle exceeds the reference angle, the observation direction decision unit 27 determines that the accuracy of specifying the position of the catheter will deteriorate.

FIG. 5A shows the position of the catheter at imaging time t2. FIG. 5B shows the position of the catheter at imaging time t3. As shown in FIG. 5A, the moving direction specifying unit 26 specifies the moving direction of the catheter based on a position P1 of the catheter at imaging time t1 and a position P2 of the catheter at imaging time t2.

The observation direction decision unit 27 specifies a blood vessel section by tracking the blood vessel in the moving direction of the catheter. The observation direction decision unit 27 specifies a comparative angle ψ2 as 30° based on the observation section and the blood vessel section. Since the comparative angle ψ2 is smaller than the reference angle, the first and second imaging systems maintain their current imaging angles.

On the other hand, referring to FIG. 5B, the observation direction decision unit 27 specifies a comparative angle ψ3 as 80°. When the comparative angle ψ3 becomes larger than the reference angle, the observation direction decision unit 27 outputs, to the display control unit 30, a signal which notifies that the comparative angle has become larger than the reference angle. The observation direction decision unit 27 specifies comparative angles respectively corresponding to a plurality of observation directions. The observation direction decision unit 27 then selects one of the plurality of observation directions in which the comparative angle becomes minimum.

Note that the observation direction decision unit 27 may execute the above processing by using the moving direction of the catheter instead of the direction of the blood vessel. In this case, the observation direction decision unit 27 specifies a section (to be referred to as a moving section hereinafter) perpendicular to the moving direction of the catheter instead of a blood vessel section. The observation direction decision unit 27 sets the angle defined by a moving section and an observation section as a comparative angle.

The image combining unit 29 generates right-eye composite image data by combining right-eye blood vessel image data and right-eye catheter image data. Likewise, the image combining unit 29 generates left-eye composite image data by combining left-eye blood vessel image data and left-eye fluoroscopic image data.

The display control unit 30 displays the right-eye composite image on the display unit 31 so as to enable the user at a predetermined position to see only the right-eye composite image with his/her right eye. The display control unit 30 also displays the left-eye composite image on the display unit 31 so as to enable the user to see only the left-eye composite image with his/her left eye. More specifically, the display control unit 30 transmits, to the display unit 31, a video signal obtained by vertically dividing the right-eye image and the left-eye image into strips.

The display unit 31 alternately arranges and displays left-eye images and right-eye images which are vertically divided into strips. The display unit 31 includes a lenticular lens on the display screen. A lenticular lens is a lens which changes the position that a line of sight reaches depending on the position at which the user sees. Therefore, the right eye of the user is made to see only a right-eye image and the left eye of the user is made to see only a left-eye image by adjusting the position at which the user visually recognizes the display unit 31 or the placement of the display unit 31.

Note that the method of displaying a right-eye image and a left-eye image is not limited to the above method as long as it is possible to realize a state in which the user sees one image with one eye and sees the other image with the other eye. In addition, any display method used in the field of stereoscopic vision can be applied as a method of displaying two images using the display control unit 30 and the display unit 31.

For example, in an eyeglass-type frame sequential scheme, the display control unit 30 transmits a right-eye image signal corresponding to a right-eye image to the display unit 31 after transmitting a left-eye image signal corresponding to a left-eye image in one frame synchronization period. The display control unit 30 repeatedly executes the above video signal transmission processing for each specific period. The display unit 31 switches and displays images for each specific period based on the left-eye image signal and the right-eye image signal repeatedly transmitted from the display control unit 30.

On the other hand, the user wears liquid crystal shutter eyeglasses and then visually recognizes the display unit 31. Liquid crystal shutters alternately shut left and right views in synchronism with image switching display processing by the display unit 31. The eyeglass shutters open and close perfectly in synchronism with two images to realize a state in which the right eye sees only a right-eye image and the left eye sees only a left-eye image.

In addition, in response to the reception of the signal which is output from the observation direction decision unit 27 to notify that the comparative angle output from the observation direction decision unit 27 has become larger than the reference angle, the display control unit 30 reads out warning message data from the storage unit 21 and displays it on the display unit 31.

The system control unit 32 includes a CPU (Central Processing Unit) and a memory circuit. The system control unit 32 receives the information input from the input unit 20, and temporarily stores the input information in the memory circuit. The system control unit 32 then controls each unit of the biplane X-ray imaging apparatus based on the input information.

For example, the system control unit 32 controls each unit to turn on an observation direction changing function (to be described later) in response to the pressing of the function ON switch of the input unit 20 and to turn off the observation direction changing function in response to the pressing of the function OFF switch.

The imaging control unit 33 executes an imaging operation by controlling the high voltage generation unit 19, an X-ray detector 13, and each driving unit based on the data of imaging conditions set in accordance with the instructions input by the user using the input unit 20. The imaging control unit 33 also controls each of the operations of the storage unit 21, the image generation unit 23, the image processing unit 24, and like in synchronism with this imaging operation.

In addition, the imaging control unit 33 controls each driving unit to move each of the first and second imaging systems to an imaging position corresponding to the observation direction selected by the observation direction decision unit 27 in response to the pressing of the change switch of the input unit 20 by the user. Note that the imaging control unit 33 may automatically move each of the first and second imaging systems to the imaging position corresponding to the selected observation direction after the execution of observation direction selection processing.

(Observation Direction Changing Function)

The observation direction changing function is a function to be executed when a comparative angle becomes larger than the reference angle. The observation direction changing function displays a warning message on the display unit 31 and selects an observation direction, from the plurality of observation directions registered in advance, in which the comparative angle becomes minimum. When the user presses the change switch, each of the first and second imaging systems is moved to the imaging position corresponding to the selected observation direction. Processing concerning the observation direction changing function (to be referred to as observation direction changing processing hereinafter) will be described next with reference to a flowchart.

Figure 6:
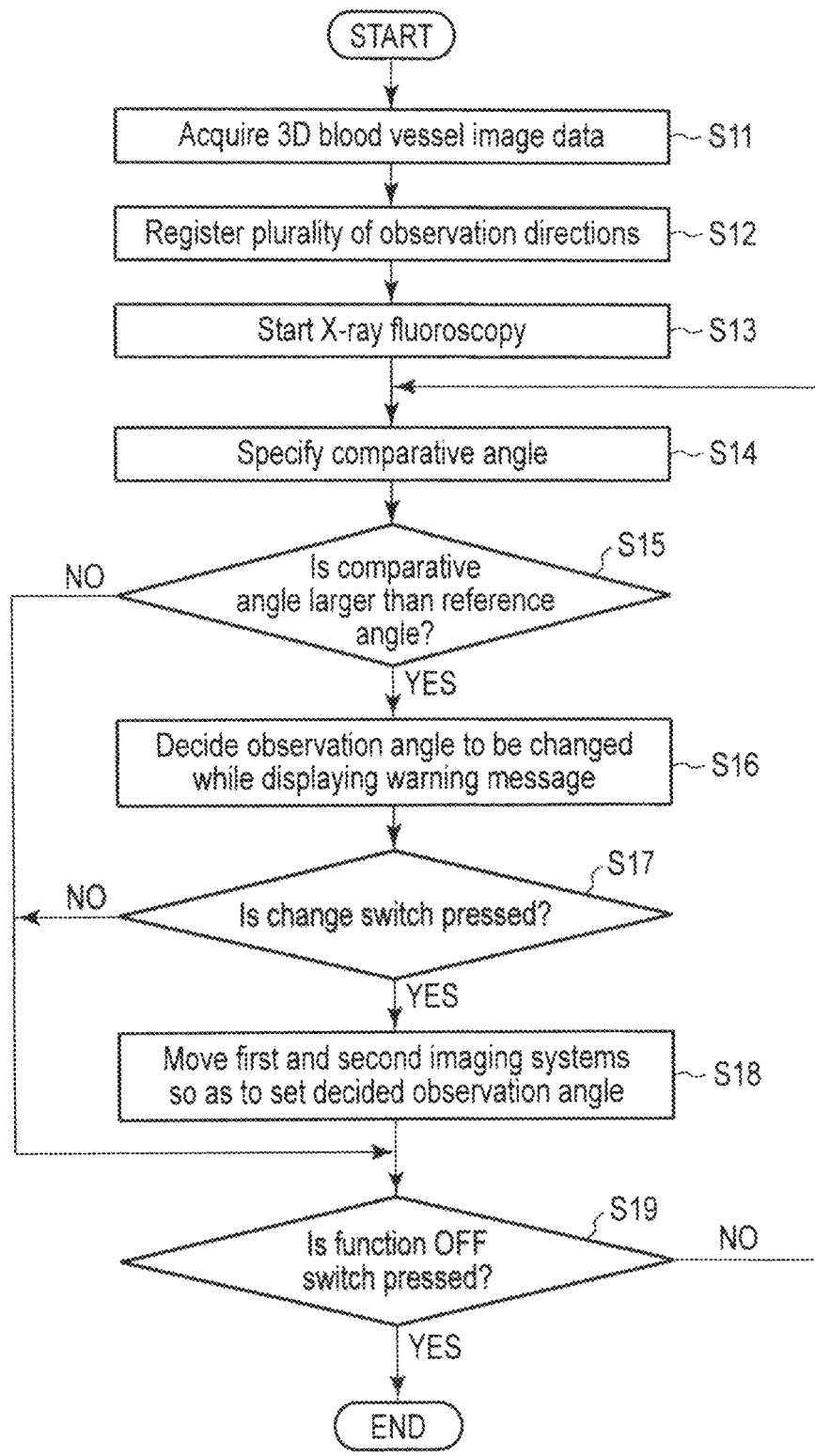
FIG. 6 is a flowchart showing an example of a processing procedure in the biplane X-ray imaging apparatus shown in FIG. 1.

FIG. 6 is a flowchart showing an example of a processing procedure by the biplane X-ray imaging apparatus shown in FIG. 1. Referring to FIG. 6, for the sake of descriptive simplicity, assume that the observation direction changing function is on.

(Step S11: Acquisition of 3D Blood Vessel Image)

The image generation unit 23 and the image processing unit 24 acquire 3D blood vessel image data.

(Step S12: Registration of Plurality of Observation Directions)

A plurality of observation directions are registered in accordance with the instructions input by the user using the input unit 20.

(Step S13: Start of X-ray Fluoroscopy)

X-ray fluoroscopy is started for the object into which the catheter is inserted.

(Step S14: Specifying of Comparative Angle)

When X-ray fluoroscopy is started, the observation direction decision unit 27 specifies a comparative angle.

(Step S15: Comparison between Comparative Angle and Reference Angle)

The observation direction decision unit 27 compares the reference angle with the comparative angle. If the result indicates that the comparative angle is equal to or less than the reference angle, the process shifts to step S19. If the comparative angle is larger than the reference angle, the process shifts to step S16.

(Step S16: Displaying of Warning Message and Decision of Observation Direction to Be Changed)

The display control unit 30 reads out warning message data from the storage unit 21. The display unit 31 then displays the message. The observation direction decision unit selects an observation direction, from the plurality of observation directions registered in advance, in which the comparative angle becomes minimum.

(Step S17: Reception of Change of Observation Direction)

The system control unit 32 monitors whether the user has pressed the change switch of the input unit 20. When the user presses the change switch, the process shifts to step S18. If the user does not press the change switch, the process shifts to step S19.

(Step S18: Change of Observation Direction)

The imaging control unit 33 drives each driving unit to move each of the first and second imaging systems to an imaging position corresponding to the observation direction selected in step S16.

(Step S19: Reception of Input from Function OFF Switch)

The system control unit 32 monitors whether the user has pressed the function OFF switch of the input unit 20. When the user presses the function OFF switch, the observation direction changing processing ends. If the user does not press the function OFF switch, the observation direction processing is continued, and the process returns to step S14.

The biplane X-ray imaging apparatus according to the first embodiment which has the observation direction changing function described above can obtain the following effects.

The biplane X-ray imaging apparatus according to the first embodiment can specify the angle (comparative angle) defined by a section (blood vessel section) perpendicular to the direction of the blood vessel along the moving direction of the catheter and a section (observation section) including the first and second imaging directions during a catheter treatment. When the comparative angle becomes larger than the reference angle, the direction of the blood vessel along the moving direction of the catheter approaches a state almost parallel to the observation section. Therefore, there is a risk that the reconstruction accuracy of the catheter may deteriorate as the catheter moves in the blood vessel.

According to the first embodiment, therefore, when a comparative angle becomes larger than the reference angle, a warning message for notifying the user that the observation direction is not suitable is displayed by the observation direction changing function. In addition, it is possible to select in advance an observation direction, from a plurality of observation directions registered, in which the comparative angle becomes minimum. Each of the first and second imaging systems can be moved to an imaging position corresponding to the selected observation direction in response to the pressing of the change switch by the user.

Therefore, the biplane X-ray imaging apparatus according to the first embodiment can move the first and second imaging systems in accordance with the direction of the blood vessel along the moving direction of the catheter. From the above, according to the first embodiment, it is possible to suppress a deterioration in the quality of a provided image caused by a change in the moving direction of the catheter in a catheter treatment.

Second Embodiment

A biplane X-ray imaging apparatus according to the second embodiment will be described next, focusing on differences from the first embodiment.

In the first embodiment, an observation direction is automatically selected from a plurality of observation directions registered in advance in accordance with the moving direction of the catheter. On the other hand, in the second embodiment, the user selects first and second imaging angles in accordance with the moving direction of the catheter.

A storage unit 21 stores the template data of an imaging angle map.

FIG. 7 is a view showing an example of the template of the imaging angle map stored in the storage unit 21 of the biplane X-ray imaging apparatus according to the second embodiment. The imaging angle map shown in FIG. 7 is a two-dimensional map in which the RAO/LAO direction is set as the abscissa, and the CRA/CAU direction is set as the ordinate. In the imaging angle map shown in FIG. 7, the user can designate 49 imaging directions from imaging direction (1) to imaging direction (49). For example, imaging direction (1) indicates that LAO is 90°, and CAU is 90°.

When the comparative angle becomes larger than the reference angle, an observation direction decision unit 27 outputs, to the display control unit 30, a signal which notifies that the comparative angle has become larger than the reference angle. In addition, the observation direction decision unit 27 calculates the angle of each of a plurality of first imaging directions with respect to the moving direction of the catheter. The observation direction decision unit 27 assigns a degree of aptitude to each of the plurality of first imaging directions in accordance with the corresponding calculated angle.

The plurality of first imaging directions are set in advance. The plurality of first imaging directions are designated by the template as indicated by, for example, the imaging angle map shown in FIG. 7.

In addition, the observation direction decision unit 27 calculates the angle of the direction of the blood vessel along the moving direction of the catheter and the angle of the first imaging direction relative to each of a plurality of second imaging directions. The observation direction decision unit 27 then assigns a degree of aptitude to each of a plurality of second imaging directions in accordance with the calculated angle of the blood vessel along the moving direction of the catheter and the calculated angle of the corresponding first imaging direction.

A display control unit 30 writes color information or gray level information corresponding to the degree of aptitude of an imaging angle on the template of the imaging angle map and causes a display unit 31 to display the template.

Figure 8A:
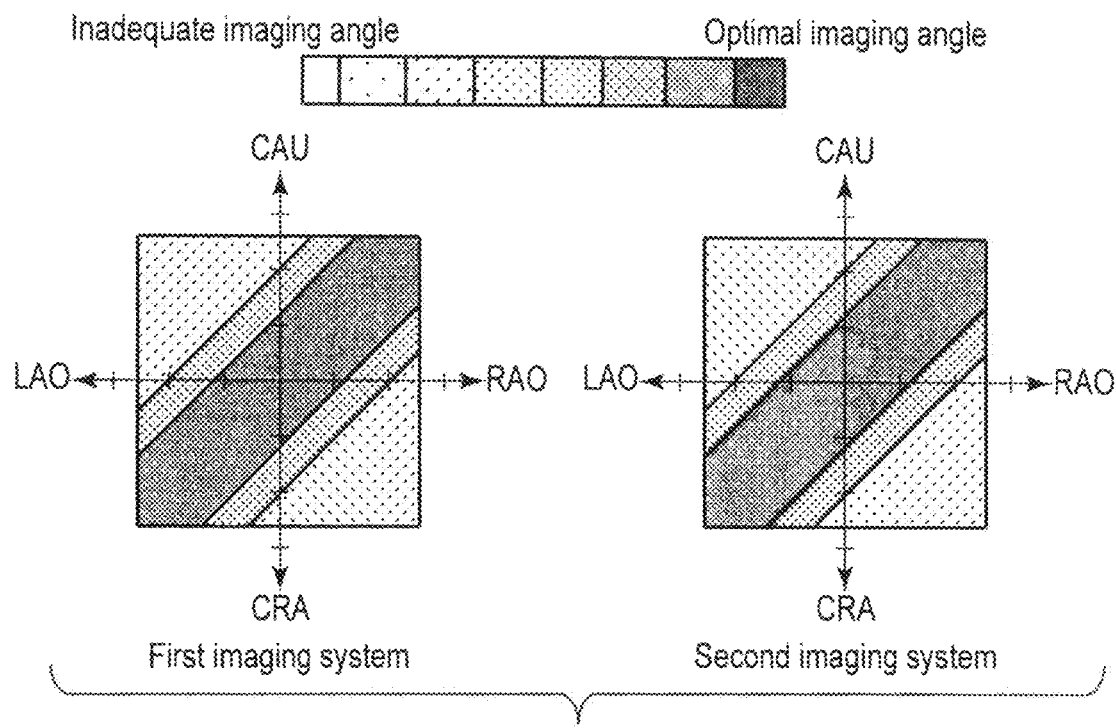
FIGS. 8A and 8B are views for explaining an imaging angle setting method in the biplane X-ray imaging apparatus according to the second embodiment.
Figure 8B:
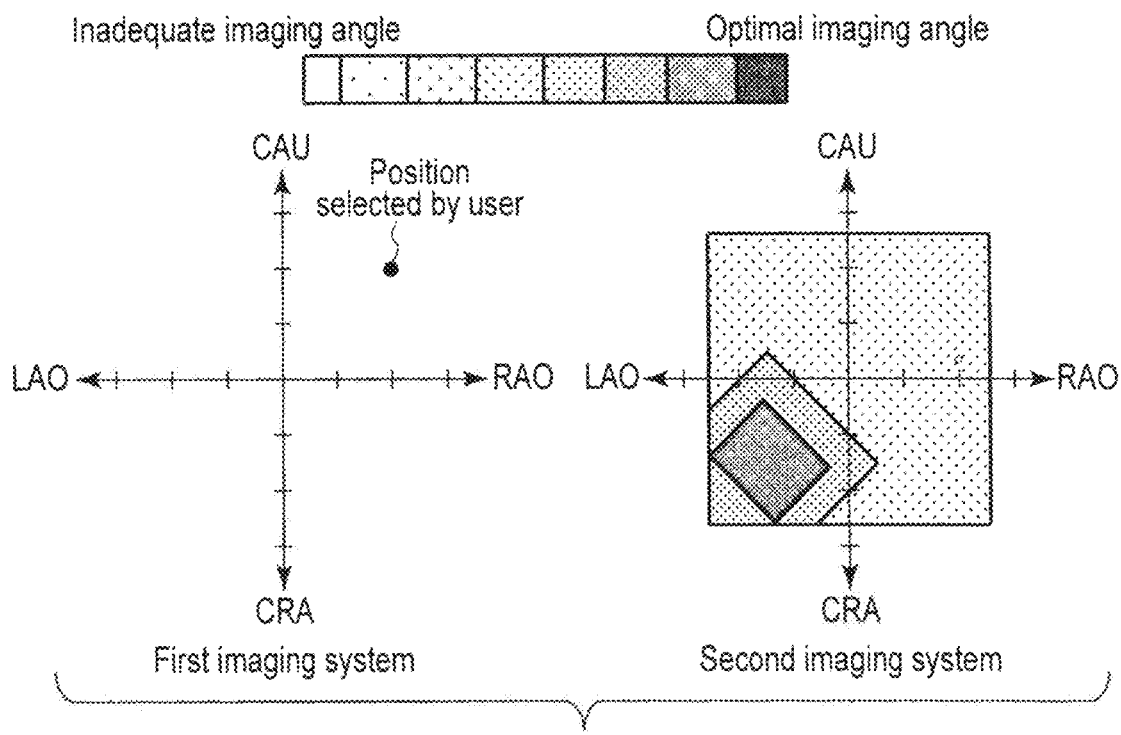

FIGS. 8A and 8B are views for explaining a method of setting an imaging angle in the biplane X-ray imaging apparatus according to the second embodiment. FIGS. 8A and 8B each show a display screen. FIG. 8A shows a screen displayed first when a comparative angle becomes larger than the reference angle.

FIG. 8A displays a first imaging angle map with which the user selects a first imaging angle, a second imaging angle map with which the user selects a second imaging angle, and a color bar corresponding to the degrees of aptitude of imaging angles. The display control unit 30 displays gray level information corresponding to the degree of aptitude of each imaging angle on both the first imaging angle map and the second imaging angle map.

The user selects a first imaging angle from the first imaging angle map displayed in FIG. 8A by a clicking operation or the like via an input unit 20. When the user selects a first imaging angle, the screen to be displayed is updated as shown in FIG. 8B.

FIG. 8B displays the first imaging direction selected by the user on the first imaging angle map. Referring to FIG. 8B, the display form of the second imaging angle map has changed. In this case, when the user selects a first imaging direction, the observation direction decision unit 27 re-assigns a degree of aptitude to each of a plurality of second imaging directions based on the moving direction of the catheter and the first imaging direction. That is, the area in the imaging direction with a high degree of aptitude, which is displayed on the second imaging angle map in FIG. 8B, is the area which is further narrowed down from the area in the imaging direction with the high degree of aptitude and is displayed on the second imaging angle map in FIG. 8A.

When the user presses the change switch of the input unit 20, an imaging control unit 33 controls each driving unit to move each of the first and second imaging systems to an imaging position corresponding to the observation direction selected by the observation direction decision unit 27. Alternatively, when the user designates first and second imaging angles on the imaging angle map displayed on the display unit 31, the first and second imaging systems are automatically moved to the imaging positions corresponding to the designated imaging angles.

The biplane X-ray imaging apparatus according to the second embodiment having the observation direction changing function described above can obtain the following effects.

The biplane X-ray imaging apparatus according to the second embodiment can display an imaging angle map on which color information or gray level information corresponding to the degree of aptitude of each imaging angle is written, when a comparative angle becomes larger than the reference angle. The user can manually set first and second imaging angles by visually recognizing an updated imaging angle map and designate the first and second imaging angles on the imaging angle map in accordance with the moving direction of the catheter or the selected one of imaging angles. From the above, according to the second embodiment, it is possible to suppress a deterioration in the quality of a provided image caused by a change in the moving direction of the catheter in a catheter treatment.

Third Embodiment

A biplane X-ray imaging apparatus according to the third embodiment will be described next, focusing on differences from the first and second embodiments.

In the first and second embodiments, the direction of a blood vessel along the moving direction of the catheter is specified. That is, the first and second embodiments are not based on the assumption of a case in which a blood vessel branches in the moving direction of the catheter. The third embodiment will exemplify processing in the biplane X-ray imaging apparatus in a case in which a blood vessel along the moving direction of the catheter branches.

When the blood vessel branches in the moving direction of the catheter specified by the moving direction specifying unit 26, an observation direction decision unit 27 specifies a blood vessel direction for each of plurality of branching blood vessels and averages the specified directions to specify an average blood vessel direction. An average blood vessel direction may be specified based on the blood vessel directions of two blood vessels of a plurality of branching blood vessels.

In the first and second embodiments, a section almost perpendicular to a blood vessel direction is set as a blood vessel section. In the third embodiment, a section almost perpendicular to an average blood vessel direction is set as a blood vessel section. In addition, the observation direction decision unit 27 according to the third embodiment selects two blood vessels from a plurality of blood vessels. A section (to be referred to as a blood vessel slice surface hereinafter) including the two selected blood vessels is specified.

Two blood vessels may be automatically selected from a plurality of blood vessels, for example, in descending order of blood vessel diameter. Obviously, it is possible to select the blood vessel designated by the user.

The observation direction decision unit 27 specifies first and second comparative angles based on the average blood vessel section and the blood vessel slice surface. The first comparative angle is the angle defined by the observation section and the blood vessel section. The second comparative angle is the angle defined by the observation section and the blood vessel slice surface.

The observation direction decision unit 27 selects an imaging direction, from a plurality of imaging directions, in which the first comparative angle is small and the second comparative angle is large. Priority levels may be set for the first and second comparative angles in advance.

If, for example, the priority level of the first comparative angle is high, the observation direction decision unit 27 selects an imaging direction, from a plurality of imaging directions, in which the first comparative angle becomes minimum. If there are a plurality of imaging directions in which the first comparative angle becomes minimum, the observation direction decision unit 27 selects an imaging direction, of the plurality of imaging directions in which the first comparative angle becomes minimum, in which the second comparative angle becomes maximum.

In addition, if the priority level of the second comparative angle is high, the observation direction decision unit 27 selects an imaging direction, from a plurality of imaging directions, in which the second comparative angle becomes almost vertical. If there are a plurality of imaging directions in which the second comparative angle becomes almost vertical, the observation direction decision unit 27 selects an imaging direction, of the plurality of imaging directions in which the second comparative angle becomes almost vertical, in which the first comparative angle becomes minimum.

In addition, the observation direction decision unit 27 may select one imaging direction from a plurality of imaging directions in accordance with a preset method. For example, the observation direction decision unit 27 selects three imaging directions from the plurality of imaging directions in ascending order of the first comparative angle, and selects an imaging direction, from the three selected imaging directions, in which the second comparative angle becomes maximum.

FIGS. 9A and 9B are views for explaining the first and second comparative angles. For the sake of descriptive simplicity, FIGS. 9A and 9B will exemplify a blood vessel having two branches.

FIG. 9A is a view for explaining the first comparative angle. The observation direction decision unit 27 specifies the first and second blood vessel directions by tracking a blood vessel along the moving direction of the catheter. The observation direction decision unit 27 specifies an average blood vessel direction by averaging the first and second blood vessel directions, and specifies a blood vessel section perpendicular to the average blood vessel direction. In addition, the observation direction decision unit 27 specifies the first comparative angle defined by an observation section corresponding to one of a plurality of imaging directions and the blood vessel section.

FIG. 9B is a view for explaining the second comparative angle. The observation direction decision unit 27 specifies the first and second blood vessel directions by tracking the blood vessel along the moving direction of the catheter. The observation direction decision unit 27 then specifies a blood vessel slice surface including the first and second blood vessel directions, and specifies the second comparative angle defined by an observation section corresponding to one of a plurality of imaging directions and the blood vessel slice surface.

Note that in a case in which the angle defined by the observation section and the perpendicular plane of the blood vessel slice surface is set as the second comparative angle, the observation direction decision unit 27 may select an imaging direction, from a plurality of imaging directions, in which the total angle obtained by adding the first comparative angle and the difference between the second comparative angle and a right angle becomes minimum.

Note that the third embodiment has exemplified the processing in the biplane X-ray imaging apparatus in the case in which the blood vessel along the moving direction of the catheter branches. The same processing can be applied to a case in which a blood vessel becomes partially deformed or swollen.

Figure 10:
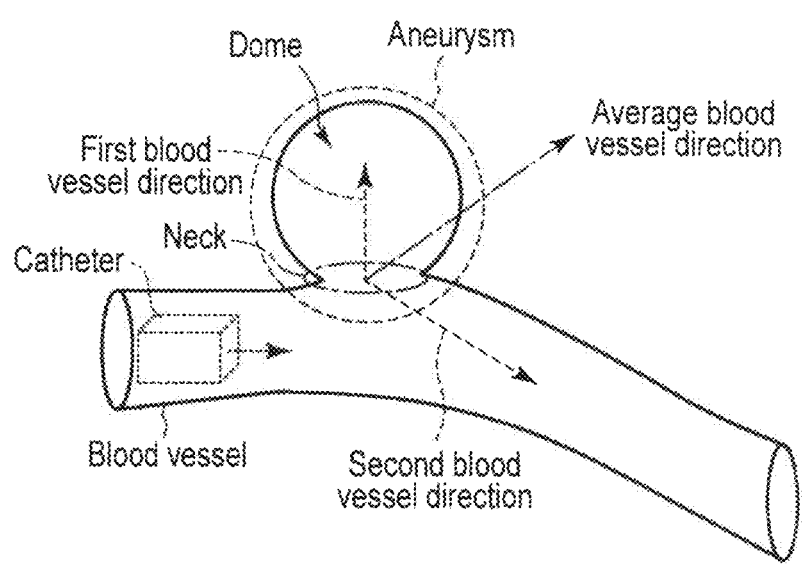
FIG. 10 is a view for explaining a blood vessel direction in a case in which an aneurysm exists in a blood vessel.

FIG. 10 is a view for explaining a blood vessel direction in a case in which there is an aneurysm in a blood vessel. As shown in FIG. 10, the observation direction decision unit 27 specifies the neck of the aneurysm by tracking the blood vessel along the moving direction of the catheter. The observation direction decision unit 27 then specifies the neck of the aneurysm as a branch, and specifies a direction from the neck of the aneurysm to the center of the dome as the first blood vessel direction. The observation direction decision unit 27 also specifies a direction from the neck of the aneurysm along the blood vessel as the second blood vessel direction.

The biplane X-ray imaging apparatus according to the third embodiment having the above observation direction changing function can obtain the following effects.

The biplane X-ray imaging apparatus according to the third embodiment can specify the presence/absence of a branch of a blood vessel in the moving direction of the catheter. The biplane X-ray imaging apparatus can move each of the first and second imaging systems to a position at which the reconstruction accuracy of the distal end portion of the catheter can be maintained, regardless of which branching blood vessel the catheter moves along. From the above, according to the third embodiment, it is possible to suppress a deterioration in the quality of a provided image caused by a change in the moving direction of the catheter in a catheter treatment.

Fourth Embodiment

A stereoscopic X-ray imaging apparatus according to the fourth embodiment will be described. The biplane X-ray imaging apparatus described in each of the first, second, and third embodiments can independently control the imaging direction of the first imaging system and the imaging direction of the second imaging system.

On the other hand, the stereoscopic X-ray imaging apparatus includes first and second imaging systems on a common C-arm 14, and hence cannot independently change the imaging direction of the first imaging system and the imaging direction of the second imaging system. The following will mainly describe the differences between the biplane X-ray imaging apparatuses according to the first, second, and third embodiments and the stereoscopic X-ray imaging apparatus according to the fourth embodiment.

Figure 11:
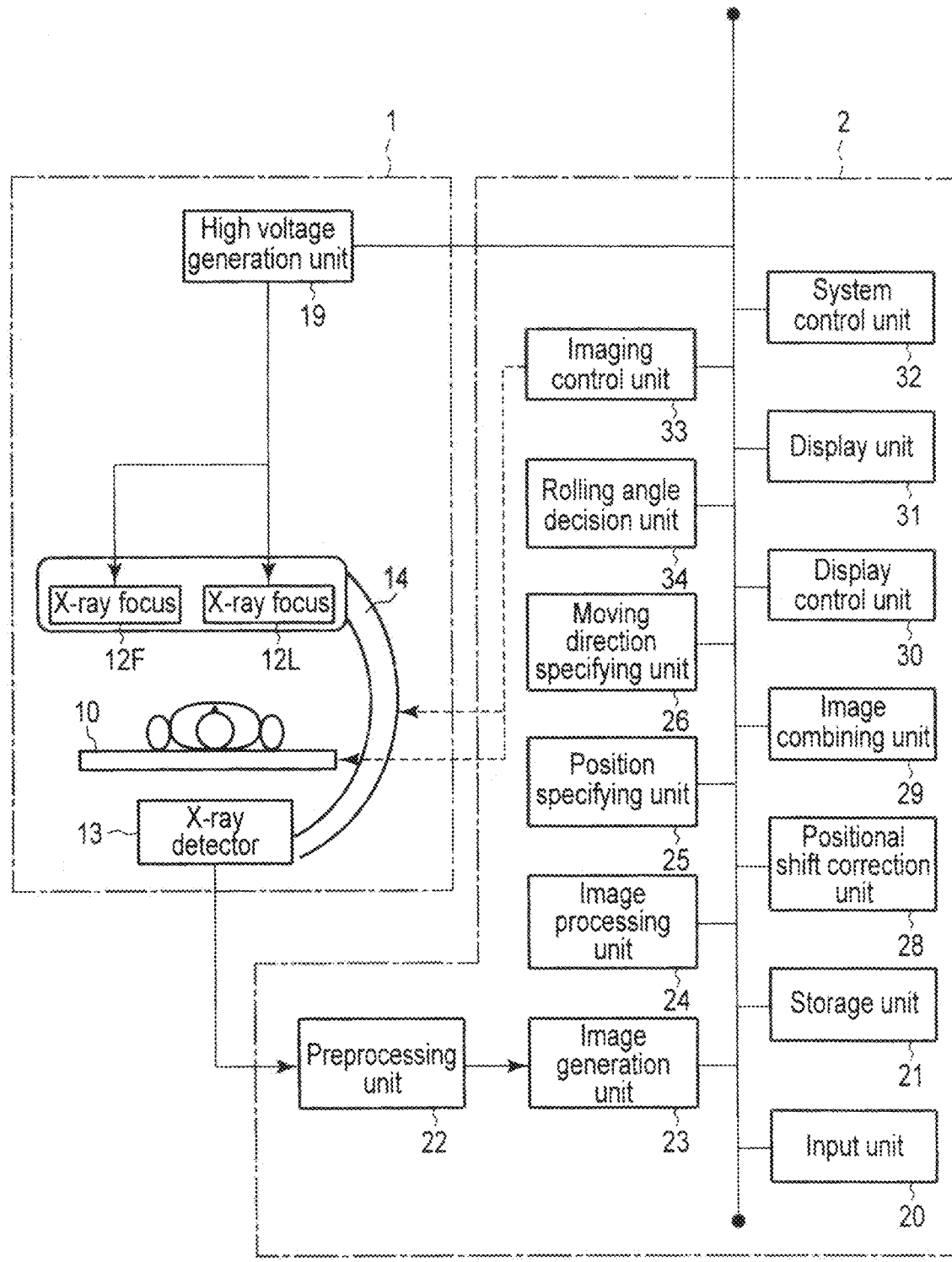
FIG. 11 is a block diagram showing an example of the arrangement of a stereoscopic X-ray imaging apparatus according to the fourth embodiment.

FIG. 11 is a block diagram showing an example of the arrangement of the stereoscopic X-ray imaging apparatus according to the fourth embodiment. The stereoscopic X-ray imaging apparatus shown in FIG. 11 includes a first X-ray focus 12F and a second X-ray focus 12L on the same C-arm 14.

In the fourth embodiment, the first imaging system includes the first X-ray focus 12F and an X-ray detector. The second imaging system includes the second X-ray focus 12L and an X-ray detector. An imaging control unit 33 controls a high voltage generation unit 19 so as to generate X-rays from the first X-ray focus 12F and the second X-ray focus 12L while switching between them. A single X-ray detector 13 detects the X-rays generated from the first X-ray focus 12F and the second X-ray focus 12L.

The image generation unit 23 generates a first fluoroscopic image corresponding to the first X-ray focus 12F and a second fluoroscopic image corresponding to the second X-ray focus 12L. An image generation unit 23 generates a plurality of X-ray image data respectively corresponding to a plurality of imaging angles concerning an object before and after the injection of a contrast medium. The imaging control unit 33 controls the high voltage generation unit 19 so as to generate X-rays from one X-ray focus while rotating the C-arm 14 around the object, and acquires a plurality of X-ray image data respectively corresponding to a plurality of imaging angles.

A storage unit 21 stores warning message data for notifying the user that the current position of the C-arm 14 is not appropriate and a plurality of rotational angle data concerning the C-arm 14.

When a comparative angle becomes larger than a reference angle, a rotating direction decision unit 34 outputs, to a display control unit 30, a signal notifying that the comparative angle has become larger than the reference angle. In addition, the rotating direction decision unit 34 specifies a comparative angle corresponding to each of a plurality of rotational angles, and selects a rotational angle, from the plurality of specified rotational angles, at which the comparative angle becomes minimum.

Upon receiving a signal notifying that the comparative angle has become larger than the reference angle from the rotating direction decision unit 34, the display control unit 30 reads out warning message data from the storage unit 21 and displays it on the display unit 31.

When the user presses the change switch of the input unit 20, the imaging control unit 33 controls each driving unit to move the C-arm 14 to the rotational angle selected by the rotating direction decision unit 34.

In the first, second, and third embodiments, an imaging direction and an observation angle can be independently set as needed. Similar settings can be made in the fourth embodiment. In addition, respectively matching the first and second imaging directions with the right eye viewing direction (or the left eye viewing direction) and the left eye viewing direction (or the right eye viewing direction) makes it possible to use catheter images obtained by extracting the movement of the catheter in different imaging directions as images in the right eye viewing direction and the left eye viewing direction. In this case, it is not always necessary to reconstruct a 3D catheter image.

The stereoscopic X-ray imaging apparatus according to the fourth embodiment having the above observation direction changing function can obtain the following effects.

When a comparative angle becomes larger than the reference angle, the stereoscopic X-ray imaging apparatus according to the fourth embodiment can display a warning message for notifying the user that the current position of the C-arm 14 is not appropriate. In addition, it is possible to select a rotational angle, from a plurality of rotational angles registered in advance, at which the comparative angle becomes minimum. When the user presses the change switch, the C-arm 14 including the first X-ray focus 12F, the second X-ray focus 12L, and the X-ray detector 13 can be moved to an imaging position corresponding to the selected rotational angle.

The stereoscopic X-ray imaging apparatus according to the fourth embodiment can therefore move the C-arm 14 to a position to maintain the accuracy of a reconstructed image of the catheter in accordance with the direction of a blood vessel along the moving direction of the catheter. From the above, according to the fourth embodiment, it is possible to suppress a deterioration in the quality of a provided image caused by a change in the moving direction of the catheter in a catheter treatment.

As has been described above, in the first to fourth embodiments, the image data of a catheter (or guide wire) is acquired from a biplane image, and the moving direction of the catheter (or guide wire) is specified based on, for example, a temporal change in the position of the distal end portion. In addition, the image data of the distal end of a catheter (guide wire) is acquired from a single plane image, and the acquired image data (the distal end portion of the catheter (or guide wire)) is back-projected on a CT image, thereby recognizing a blood vessel nearest to the distal end as a distal end position. It is then possible to specify the moving direction of the catheter (guide wire) by specifying a blood vessel running direction at the distal end position.

While certain embodiments have been described, these embodiments have been presented by way of example only, and are not intended to limit the scope of the inventions. Indeed, the novel embodiments described herein may be embodied in a variety of other forms; furthermore, various omissions, substitutions, and changes in the form of the embodiments described herein may be made without departing from the spirit of the inventions. The accompanying claims and their equivalents are intended to cover such forms or modifications as would fall within the scope and spirit of the inventions.

The invention claimed is:

1. An X-ray diagnosis apparatus, which is configured to image an object into which a device is inserted, the object being imaged from a first imaging direction and a second imaging direction, the X-ray diagnosis apparatus comprising:
    a first X-ray source;
    a first X-ray detector;
    a first arm holding the first X-ray source and the first X-ray detector movably about a plurality of axes, and determining the first imaging direction;
    a second X-ray source;
    a second X-ray detector;
    a second arm holding the second X-ray source and the second X-ray detector movably about a plurality of axes, and determining the second imaging direction; and
    processing circuitry configured to:
        generate, based on an output from the first X-ray detector, first image data corresponding to the first imaging direction, and, based on an output from the second X-ray detector, second image data corresponding to the second imaging direction,
        specify a three-dimensional position of a distal end of the device based on the first image data and the second image data by reconstructing a three-dimensional device image data,
        specify a moving direction in a three-dimensional space of the device based on a plurality of positions of the distal end of the device, which are specified based on a plurality of first images of the first image data generated at different times and a plurality of second images of the second image data generated at the different times, the plurality of positions of the device including the specified three-dimensional position of the distal end of the device based on the first image data and the second image data, and
        control a first imaging angle corresponding to the first imaging direction and a second imaging angle corresponding to the second imaging direction in accordance with the moving direction of the device by controlling the first aim and the second arm.

2. The X-ray diagnosis apparatus of claim 1, further comprising a memory configured to store data of a plurality of imaging angle sets, the plurality of imaging angle sets including the first imaging angle and the second imaging angle, wherein
    the processing circuitry is further configured to set the first imaging angle by selecting one imaging angle set from the plurality of imaging angle sets stored in the memory.

3. The X-ray diagnosis apparatus of claim 2, wherein the processing circuitry is further configured to select an imaging angle set, from a plurality of imaging angle sets, which minimizes a sum of errors between a first angle and a second angle, wherein
    the first angle is an angle defined by a cross section of a first blood vessel nearly perpendicular to an average blood vessel direction of a plurality of branching blood vessels along a moving direction of the device and a cross section of the first blood vessel that is defined by the first imaging direction and the second imaging direction, and the second angle is an angle defined by a cross section of a second blood vessel perpendicular to a cross section of two blood vessels of the plurality of branching blood vessels and a cross section of the second blood vessel that is defined by the first imaging direction and the second imaging direction.

4. The X-ray diagnosis apparatus of claim 1, wherein the processing circuitry is further configured to select a set of imaging angles from a plurality of imaging angle sets, each set of imaging angles including the first imaging angle and the second imaging angle, the selected set of imaging angles minimizing an angle defined by a first plane estimated to be perpendicular to the moving direction of the device or a blood vessel along a moving direction of the device and a second plane including the first imaging direction and the second imaging direction, the blood vessel being a blood vessel of the object.

5. The X-ray diagnosis apparatus of claim 1, wherein the processing circuitry is further configured to select an imaging angle set, from a plurality of imaging angle sets, which minimizes an angle defined by a first cross section of a blood vessel nearly perpendicular to an average blood vessel direction of a plurality of branching blood vessels along a moving direction of the device and a second cross section of the blood vessel that is defined by the first imaging direction and the second imaging direction.

6. The X-ray diagnosis apparatus of claim 1, wherein the processing circuitry is further configured to select one imaging angle set from a plurality of imaging angle sets based on a first angle and a second angle, wherein the first angle is an angle defined by a cross section of a blood vessel nearly perpendicular to an average blood vessel direction of a plurality of branching blood vessels along a moving direction of the device and a cross section of the blood vessel that is defined by the first imaging direction and the second imaging direction, and the second angle is an angle defined by a cross section of two branching blood vessels of the plurality of branching blood vessels and a cross section of the two branching blood vessels that is defined by the first imaging direction and the second imaging direction.

7. The X-ray diagnosis apparatus of claim 6, wherein the processing circuitry is further configured to narrow down the plurality of imaging angle sets in ascending order of the first angle, and select an imaging angle set, of the plurality of narrowed down imaging angle sets, Which maximizes the second angle.

8. The X-ray diagnosis apparatus of claim 6, wherein the processing circuitry is further configured to narrow down the plurality of imaging angle sets in descending order of the second angle, and select an imaging angle set, of the plurality of narrowed down imaging angle sets, which minimizes the first angle.

9. The X-ray diagnosis apparatus of claim 6, wherein a branching position of the two branching blood vessels is a central position of a neck of an aneurysm, and one branching blood vessel of the two branching blood vessels is a blood vessel running from the branching position to a center of a dome of the aneurysm.

10. The X-ray diagnosis apparatus of claim 1, wherein the processing circuitry is further configured to control the first arm and the second arm so as to move the first X-ray source, the first X-ray detector, the second X-ray source, and the second X-ray detector to a position corresponding to an imaging angle set, the imaging angle set being selected in accordance with an instruction from a user.

11. The X-ray diagnosis apparatus of claim 1, further comprising a biplane X-ray imaging apparatus including a first imaging system configured to perform imaging in the first imaging direction to generate the first image data, and a second imaging system configured to perform imaging in the second imaging direction to generate the second image data, wherein the first imaging system includes the first arm, the first X-ray source, and the first X-ray detector, and the second imaging system includes the second arm, the second X-ray source, and the second X-ray detector.

12. The X-ray diagnosis apparatus of claim 1, further comprising an imaging apparatus which includes a stereoscopic tube with a first X-ray focus and a second X-ray focus and detects generated X-rays with one X-ray detector while switching between the first X-ray focus and the second X-ray focus.

13. The X-ray diagnosis apparatus of claim 1, wherein the processing circuitry is further configured to generate a plurality of image data of the object at a plurality of angles including the first imaging angle and the second imaging angle, the plurality of image data of the object including the first image data and the second image data, and the first image data and the second image data capturing at least a portion of the device.

14. The X-ray diagnosis apparatus of claim 13, wherein the processing circuitry is further configured to generate a three-dimensional image of the object reconstructed from the plurality of image data of the object.

15. The X-ray diagnosis apparatus of claim 14, wherein the processing circuitry is further configured to set both the first imaging angle and the second imaging angle based on tracking, within the three-dimensional image of the object, the moving direction of the device.

16. The X-ray diagnosis apparatus of claim 1, wherein the processing circuitry is further configured to generate, based on the three-dimensional device image data, device image data for a right eye and device image data for a left eye, the device image data for the right eye and the device image data for the left eye to be used in a display method of an image stereoscopic vision, wherein the device image data for the right eye corresponds to a right-eye viewing direction, and the device image data for the left eye corresponds to a left-eye viewing direction.

* * * * *